US009066675B2

(12) United States Patent
Mori

(10) Patent No.: US 9,066,675 B2
(45) Date of Patent: Jun. 30, 2015

(54) COLLIMATOR, MANUFACTURING METHOD OF COLLIMATOR, AND X-RAY CT DEVICE

(75) Inventor: Kazuhiko Mori, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 355 days.

(21) Appl. No.: 13/607,385

(22) Filed: Sep. 7, 2012

(65) Prior Publication Data

US 2013/0070892 A1 Mar. 21, 2013

(30) Foreign Application Priority Data

Sep. 20, 2011 (JP) ................ P2011-205392

(51) Int. Cl.
*A61B 6/06* (2006.01)
*G21K 1/02* (2006.01)
*A61B 6/03* (2006.01)

(52) U.S. Cl.
CPC .............. *A61B 6/06* (2013.01); *Y10T 29/49826* (2015.01); *A61B 6/032* (2013.01); *G21K 1/025* (2013.01)

(58) Field of Classification Search
CPC ............ A61B 6/03; A61B 6/032; A61B 6/06; G21K 1/02; G21K 1/025
USPC .......................................... 378/19, 147–153
See application file for complete search history.

(56) References Cited

U.S. PATENT DOCUMENTS

| 5,099,134 | A | * | 3/1992 | Hase et al. ................ 250/505.1 |
| 6,134,301 | A | | 10/2000 | Mruzek |
| 6,707,884 | B1 | * | 3/2004 | Ogawa .......................... 378/154 |
| 2003/0223548 | A1 | | 12/2003 | Galish et al. |
| 2007/0064878 | A1 | * | 3/2007 | Heismann ..................... 378/154 |
| 2007/0071163 | A1 | * | 3/2007 | Sakuta ............................ 378/19 |
| 2010/0239072 | A1 | * | 9/2010 | Kurochi ....................... 378/147 |

FOREIGN PATENT DOCUMENTS

| JP | 04002989 | 1/1992 |
| JP | 2918901 B2 | 7/1999 |
| JP | 2010-130433 | 6/2010 |
| JP | 201164625 | 3/2011 |

OTHER PUBLICATIONS

Search Report from EP12184645.5 dated Jan. 17, 2013.

\* cited by examiner

*Primary Examiner* — Robert Kim
*Assistant Examiner* — David E Smith
(74) *Attorney, Agent, or Firm* — Patterson & Sheridan, LLP

(57) ABSTRACT

A collimator includes a plurality of first plate-shaped parts, and a plurality of second plate-shaped parts interlocking with the plurality of first plate-shaped parts. Each of the plurality of first plate-shaped parts and the plurality of second plate-shaped parts arranged with a rectangular spacing therebetween and form a grid-like pattern. Each of the first plate-shaped parts comprises a first slotted plate part having a plurality of first slits formed thereon that is fixed to each of the second plate-shaped parts. A second slotted plate part having a plurality of second slits formed thereon is coupled to a side of the second plate-shaped parts opposite to the first slotted plate part. An adjustment plate part is disposed between the first slotted plate part and the second slotted plate part.

12 Claims, 6 Drawing Sheets

COLLIMATOR, MANUFACTURING METHOD OF COLLIMATOR, AND X-RAY CT DEVICE

CROSS-REFERENCE TO RELATED APPLICATION

This application is based upon and claims the benefit of priority from Japanese Patent Application No. 2011-205392, filed Sep. 20, 2011; the entire contents of which are incorporated herein by reference.

FIELD

Embodiments described herein relate to a collimator, a manufacturing method of a collimator, and an X-ray CT device.

BACKGROUND

In an X-ray computer tomography (CT) device, an X-ray detector using a scintillator is adopted in order to increase the spatial resolution with an increased number of detecting points.

Here, in order to meet the demand of producing high resolution images in a wide range and at a high speed, an X-ray detector equipped with plural photoelectric converting elements in both a channel direction and a slice direction is adopted. For such an X-ray detector, when the number of photoelectric converting elements in the slice direction is increased, it is necessary to mitigate the scattered X-rays not only in the channel direction, but also in the slice direction.

For this purpose, a type of collimator in which plural elements, each of which is prepared by monolithically molding a plate-shaped base portion and plural wall portions protruding from the base portion, are laminated has been proposed.

For the conventional collimator, when the plate-shaped base portion and plural wall portions protruding from the base portion are formed from a monolithic plate material, the plural wall portions are prone to deformation due to the fitting resistance between the plural wall portions and the base portion. Such a collimator is unstable, making it difficult to carry out image detection and measurement with high precision.

DESCRIPTION OF THE DRAWINGS

FIG. 4A is a schematic perspective view illustrating an example of the structure of the collimator. FIG. 4B is a schematic exploded view of the collimator of FIG. 4A.

FIG. 5A is a diagram illustrating a plate-shaped part 11, and FIG. 5B is a diagram illustrating a plate-shaped part 21.

DETAILED DESCRIPTION

Figure 1:
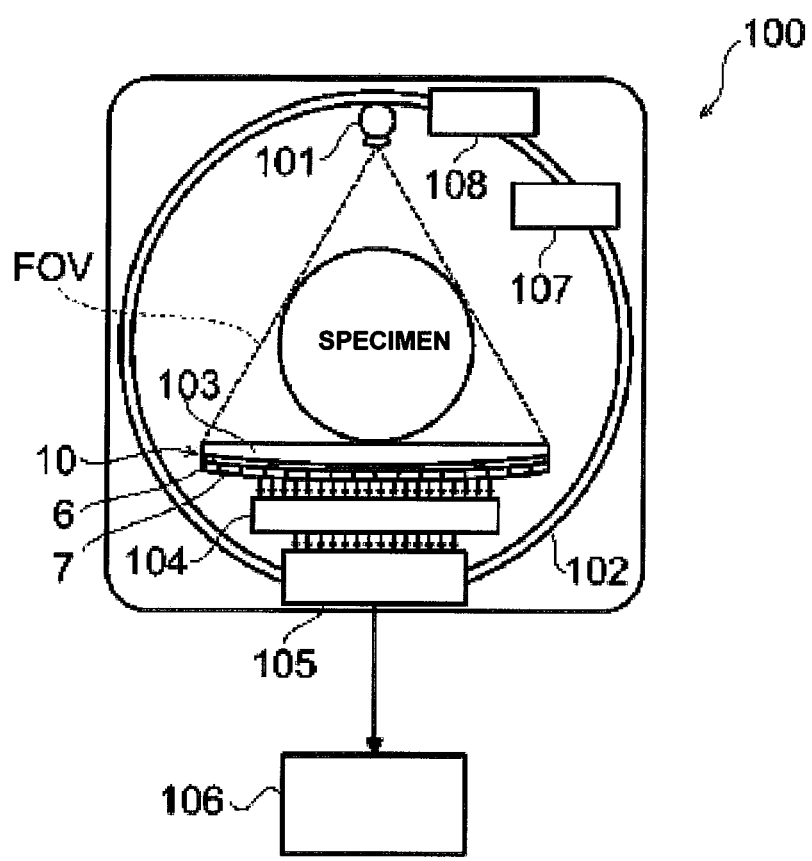
FIG. 1 is a schematic view illustrating an X-ray CT device according to one embodiment.

In general, the embodiments will be explained with reference to figures. The same reference numerals are adopted throughout the various figures, and common reference numerals will not be explained in detail. In the following, as an example, the case in which X-rays are the radiation rays will be explained. However, the apparatus, methods and techniques disclosed herein may also be adopted for other radiation rays, such as γ rays, etc.

According to one embodiment, there is provided a collimator, a manufacturing method of a collimator, and an X-ray CT device that allows measurement at a higher precision.

In order to achieve high measurement precision as well as structural stability, the collimator according to the embodiment has first plate-shaped parts arranged with even spacing therebetween, and second plate-shaped parts arranged with even spacing therebetween. The first and second plate-shaped parts are constructed to form multiple perpendicular junctions where the first and second plate-shaped parts intersect. Each of the first plate-shaped parts has a first slotted plate part having plural first slits formed thereon, a second slotted plate part having plural second slits formed thereon and arranged on a side opposite the first slotted plate part, and an adjusting part arranged between the first slotted plate part and the second slotted plate part, the plural second plate-shaped parts each have plural third slits formed thereon.

A manufacturing method of the collimator according to the embodiment has the following operations: an operation in which the first slotted plate part having plural first slits formed thereon is inserted in the plural third slits of the second plate-shaped part and they are fit with each other, an operation in which the second slotted plate part with plural second slits formed thereon is inserted in the plural third slits of the second plate-shaped part and they are fit with each other, and an operation in which the adjusting part is arranged as it is inserted into between the first slotted plate part and the second slotted plate part.

An X-ray CT device according to the embodiment has an X-ray source that emits X-rays as the radiation rays, a radiation ray detector, which has a collimator according to the embodiments, scintillators that receive the X-rays and emit fluorescence, and a photoelectric converting part that converts the fluorescence into an electric signal. A rotating ring is used to support the X-ray source and the radiation ray detector and rotates around a specimen, and a processing part that restructures the tomographic picture of the specimen on the basis of the intensity of the X-rays detected by the radiation ray detector.

Figure 2:
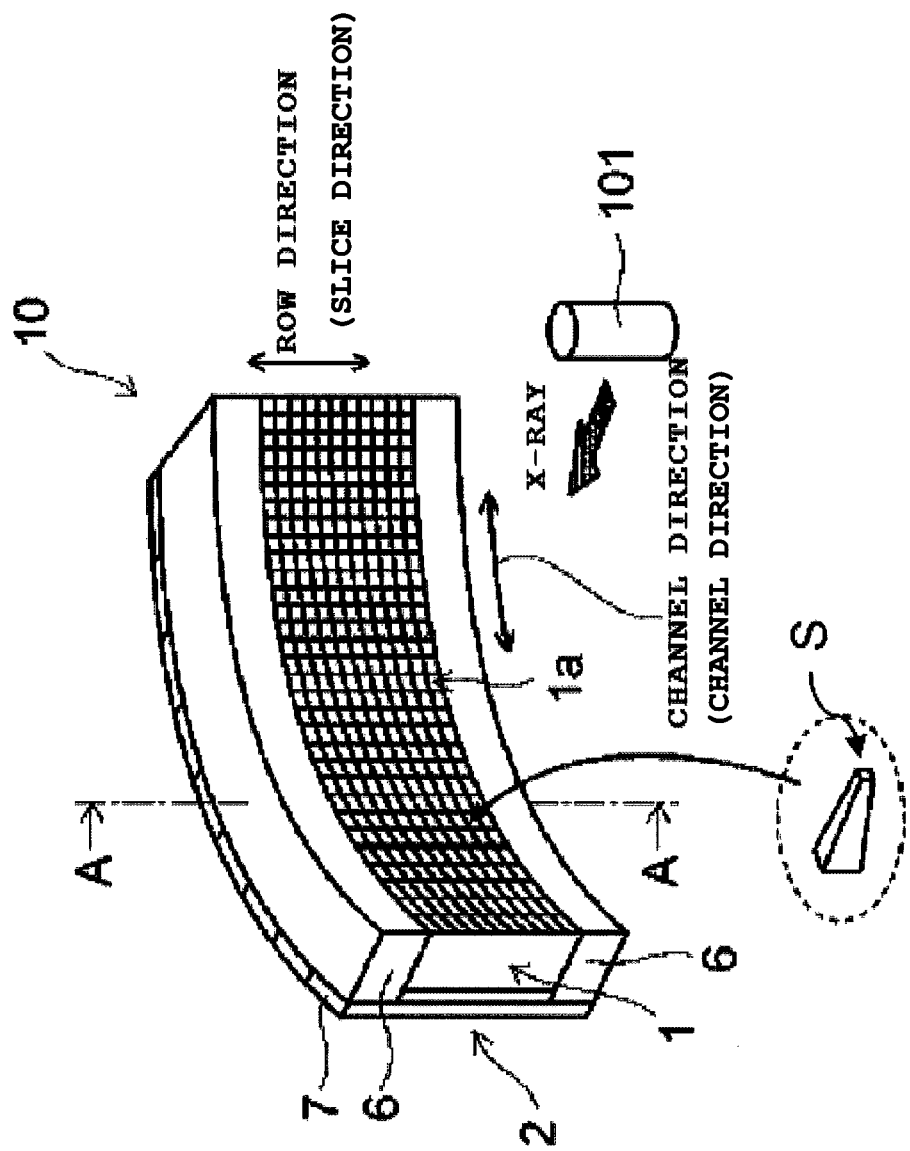
FIG. 2 is a schematic perspective view illustrating an example of a radiation ray detector related to the X-ray CT device of FIG. 1.

Referring to FIGS. 1 and 2, a collimator 1 and an X-ray CT device 100 will be explained. FIG. 1 is a schematic block diagram illustrating the configuration of an example of the X-ray CT device 100 having a radiation detector 10 comprising the collimator 1.

As shown in FIG. 1, the X-ray CT device 100 has the following parts: an X-ray bulb 101, a rotating ring 102, a two-dimensional detecting part 103, a data acquisition system (DAS) 104, a non-contact data transmission device 105, a table driving part 107, a slip ring 108, and a processor 106.

The X-ray bulb 101 as the X-ray source for emitting X-rays may be a vacuum bulb that emits X-rays. The X-ray bulb 101 is supported on the rotating ring 102. The electric power (tube current, tube voltage) needed for emitting the X-rays is provided from a high voltage generator (not shown) and is provided via the slip ring 108 attached thereto. Within the X-ray bulb 101, electrons are accelerated by the applied high voltage hit an anode, thereby causing X-rays to be emitted towards the specimen within an effective field of view (FOV).

Between the X-ray bulb 101 and the specimen, there may be beam optics and/or an X-ray collimator (not shown) for shaping the X-ray beam emitted from the X-ray bulb 101 to a desired beam shape. The beam shape may be a conical shape, a rectangular or square shape, a fan beam shape or the like.

Figure 3:
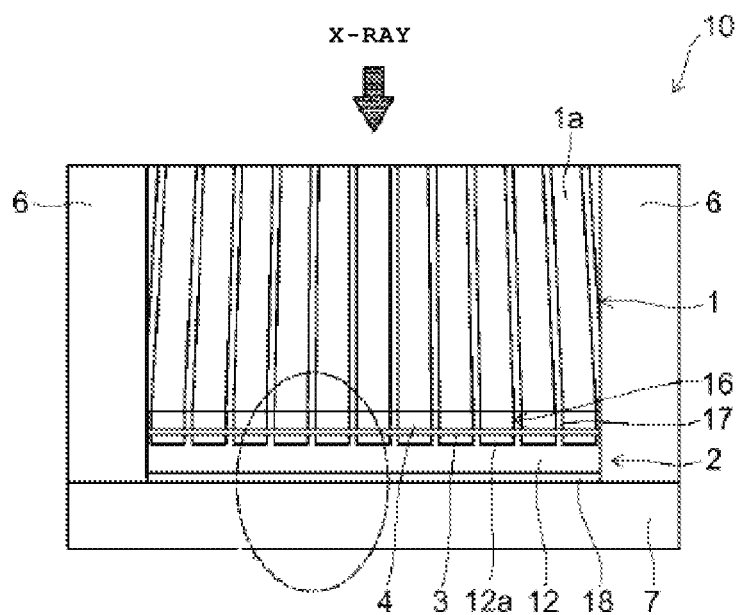
FIG. 3 is a schematic cross-sectional view taken along line A-A of FIG. 2.

Referring to FIGS. 1-3, the two-dimensional detecting part 103 is a detector system for detecting the X-rays that have propagated through the specimen. It is supported on the rotating ring 102 via a holding part 6 and a base part 7 to face the X-ray bulb 101. On the outer peripheral side (i.e., the side opposite to the specimen) of the two-dimensional detecting part 103, the radiation ray detector 10 is attached. The radiation ray detector 10 comprises the collimator 1, scintillators 4 (shown in FIG. 3) that receive the X-rays and emit fluorescence in response to the X-rays, and a photoelectric converting part 12 (shown in FIG. 3) that converts the fluorescence into an electric signal. Details regarding the collimator 1 will be explained in FIGS. 2 and 3.

The X-ray bulb 101 and two-dimensional detecting part 103 are supported on the rotating ring 102. This rotating ring 102 is driven by the table driving part 107 so that it rotates around the specimen.

The DAS 104 has plural data acquisition element rows in which DAS chips are arranged. The data corresponding to the X-rays detected by the two-dimensional detecting part 103 (hereinafter referred to as raw data) is inputted to the DAS 104. After an amplification process and analog-to-digital (A/D) conversion process, etc., the raw data are sent to the processor 106 via the data transmission device 105.

The table driving part 107 carries out driving and control so that the X-ray bulb 101 and the two-dimensional detecting part 103 are rotated at an equal speed around an axis of the X-ray CT device 100. Although not labeled, the axis is generally perpendicular to the cross-section of FIG. 1 and near the center of the rotating ring 102.

The processor 106 carries out correction for the sensitivity of the raw data and correction for the X-ray intensity to form "projection data". The projection data are reconstructed based restructuring parameters (restructuring region size, restructuring matrix size, threshold for extracting the portion concerned, etc.) to provide reconstructed video data for the slice portions.

For the restructured video data, window conversion, red, green, blue (RGB) processing, and other image processes for display is performed, and the resulting image is output to a display unit not shown in the figure. Generally, the processor 106 reconstructs the tomogram of the specimen on the basis of an X-ray intensity detected by the radiation ray detector 10.

FIG. 2 is a schematic perspective view illustrating an example of the radiation ray detector 10. FIG. 3 is a schematic cross-sectional view taken along line A-A in FIG. 2.

As shown in FIG. 2, the radiation ray detector 10 has a detector 2 and the collimator 1. In addition, the radiation ray detector 10 is supported on the periphery of the two-dimensional detecting part 103 by holding parts 6 which are arranged on the two-dimensional detecting part 103.

As shown in FIG. 2, the collimator 1 comprises a lattice structure formed of a plurality of interlocking X-ray shielding plates (e.g., plate-shaped parts 11, 21 to be explained later) that shields the X-rays, and various divisions la of the lattice structure have a structure corresponding to the various divisions of the scintillator 4. In this case, the lattice structure of the collimator 1 is such that when the collimator 1 is arranged at the position in the X-ray CT device 100 shown in FIG. 1, the various divisions la of the collimator 1 are oriented in the direction towards the focal point of the X-ray bulb 101 (e.g., X-ray source).

For example, as shown in FIG. 2, the collimator 1 may be configured such that each division la includes a rectangular shape as viewed from the perspective of the X-ray bulb 101.

With such a lattice structure, in the channel direction and the slice direction, the various X-ray shielding plates that form the various divisions la are inclined at an angle in the direction towards a common point, which may be the focal point of the X-ray bulb 101 when the collimator 1 is arranged at the proper position in the X-ray CT device 100 shown in FIG. 1. The structure of the X-ray shielding plates of the collimator 1 will be explained later.

Also, as shown in FIG. 3, the detector 2 has the following parts arranged in it: scintillators 4, an optical reflector 17, a bonding layer 3, a photoelectric converting part 12, a circuit board 18, and a base part 7.

The scintillator 4 is separated into divisions that correspond to the divisions la of the collimator 1. The divisions of the scintillator 4 also correspond to the detecting divisions of the photoelectric converting element 12a arranged in the photoelectric converting part 12, with gaps 16 formed between the various detecting divisions of the photoelectric converting element 12a. In other words, the scintillator 4 is divided by gaps 16 to separate the scintillator 4 into distinct divisions or component parts. However, the scintillator 4 and the photoelectric converting part 12 are bonded together so that the corresponding detecting divisions of the photoelectric converting element 12a are in communication with the divisions of the scintillator 4.

The scintillator 4 is arranged facing the collimator 1, and it emits fluorescence when receiving X-rays or other radiation rays. Here, the fluorescence may be visible light or other light rays. Depending on the specific material, the scintillator 4 has different maximum light emission wavelengths, decay times, reflectivity, density, temperature dependence of the optical output ratio, fluorescence efficiency, etc. Consequently, one may select different materials corresponding to different applications. For example, when an X-ray CT device is to be used, one may use a ceramic scintillator made of a sintered body of rare earth acid sulfide. However, the materials of the scintillator 4 is not limited to this material and one may adopt other materials, as appropriate, for other wavelengths.

In the gaps 16 between the scintillators 4, the optical reflecting part 17 is made of a material (such as white plate-shaped body or the like) that can reflect light at the wavelength near the emitted light wavelength of the scintillator 4 may be inserted and bonded.

The optical reflecting part 17 that divides the scintillator 4 into each photoelectric converting element 12a can perform optical separation and reflection between the divisions of the various scintillators 4, so that it can suppress the optical crosstalk between the various divisions of the scintillators 4.

The photoelectric converting part 12 has photoelectric converting element 12a that converts the fluorescence emitted from the scintillator 4 into an electric signal. As the photoelectric converting element 12a, for example, one may use a p-i-n-structure, a silicon photodiode, or the like.

The bonding layer 3 maybe made of a transparent adhesive, and it is utilized to bond the scintillator 4 and photoelectric converting part 12 with each other, and provides an excellent light transmission effect between the scintillator 4 and the photoelectric converting part 12.

The circuit board 18 is bonded with the scintillator 4 between the photoelectric converting part 12 and the base part 7. The circuit board 18 may also be separated into divisions corresponding to the divisions of the scintillator 4 for accumulating the electric signals from the various divisions of the scintillator 4.

The base part 7 has a plate-shape. On its principal surface, the circuit board 18, photoelectric converting part 12, bonding layer 3, and scintillator 4 having the optical reflecting part 17 formed thereon are arranged so as to be laminated thereto. Also, by means of the screws or other fastening parts not shown in the figure, the base part 7 is attached to the holding parts 6. Consequently, as the holding parts 6 are attached on the base part 7, the laminated scintillator 4, and other components formed on the base part 7, can be held in position by the holding parts 6.

The holding parts 6 are arranged in the two-dimensional detecting part 103 for holding the radiation ray detector 10 having the various divisions of the scintillators 4 set in a sector form facing the focal point of the X-ray source (e.g., X-ray bulb 101). A pair of holding parts 6 is arranged facing each other with a spacing between them, and the collimator 1 is held between the holding parts 6. In this case, for example, the collimator 1 may be bonded by an adhesive between the holding parts 6 so that the collimator 1 is held in the holding parts 6. Of course, the holding method of the collimator 1 is not limited to using an adhesive and other fastening methods may be appropriately used. For example, one may also use an arrangement in which the collimator 1 is fit in a trench or the like, not shown in the figure, so that the collimator 1 is held by the holding parts 6.

Referring to FIG. 2, on the outer peripheral side of the pair of holding parts 6 (i.e., the convex side of the sector shaped radiation ray detector 10), the base part 7 arranged on the detector 2 is held. Collimator 1 is the same shape as the convex holding parts 6 and is secured between these holding parts 6. Also, a plurality of base parts 7 may be arranged along the outer peripheral surface of the radiation ray detector 10 to correspond to the shape of the outer peripheral side of the holding part 6.

In the following, an example of the collimator 1 will be presented. As shown in FIG. 2, the collimator 1 has a lattice structure across the row direction and the channel direction where the X-rays emitted from the X-ray bulb 101 pass. The lattice structure has divisions la formed in a rectangular cross-sectional shape. In one aspect, the cross-sectional area of each division 1a increases as the position of the divisions 1a becomes farther from the position of the X-ray bulb 101. Here, for example, as shown in FIG. 2, the lattice structure may have each rectangular division in a square cross-sectional shape. FIG. 2 shows an example of a structure S which is the form of the space of each of the divisions 1a.

Also, as shown in FIG. 3, the collimator 1 can control the X-rays incident on each scintillator 4 and, at the same time, effectively prevents transmission of the scattered X-rays to decrease the crosstalk caused by the scattered X-rays.

Examples of the materials for forming the collimator 1 include W (tungsten), Mo (molybdenum), Ta (tantalum), Pb (lead), and alloys containing at least one of the heavy metals. However, the collimator 1 is not limited to these types of materials. One may select appropriate types of materials with excellent X-ray shielding characteristics that effectively prevent X-rays, or other high energy wavelengths, from passing therethrough.

As will be explained later, the lattice structure of the collimator 1 may also comprise a plurality of modular lattice units (or block units) arranged and combined to form the lattice structure. In this case, for the lattice structure of the module units, the various divisions la of the lattice structure are aligned so that they face the focal point of the X-ray bulb 101 (i.e., X-ray source), while the modular units are arranged side-by-side in the holding parts 6 (i.e., supporting parts).

The lattice structure of the module units is formed to ensure that they can be quickly and easily connected/disconnected with respect to the holding parts 6.

Figure 4A:
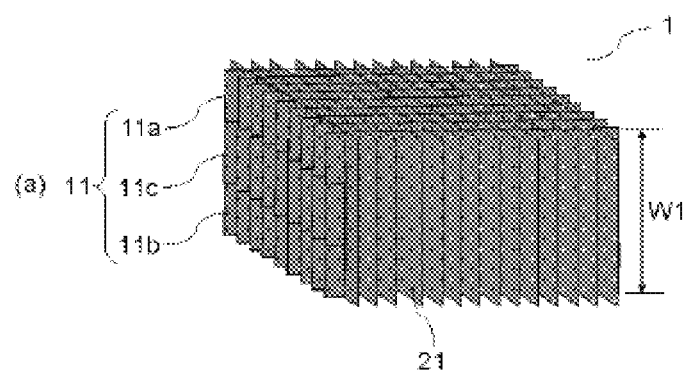
FIGS. 4A and 4B illustrate embodiments of the structure of a collimator.
Figure 4B:
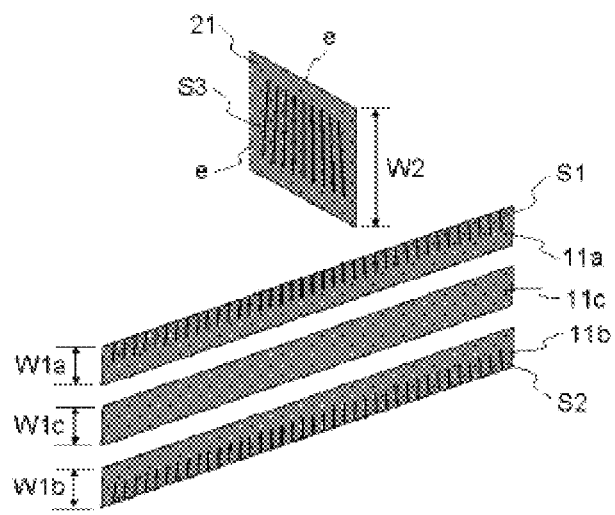
Figure 5A:
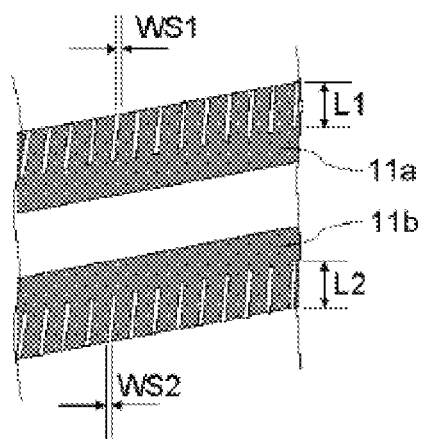
FIGS. 5A and 5B illustrate embodiments of plate-shaped parts that form the collimator of FIGS. 4A and 4B.
Figure 5B:
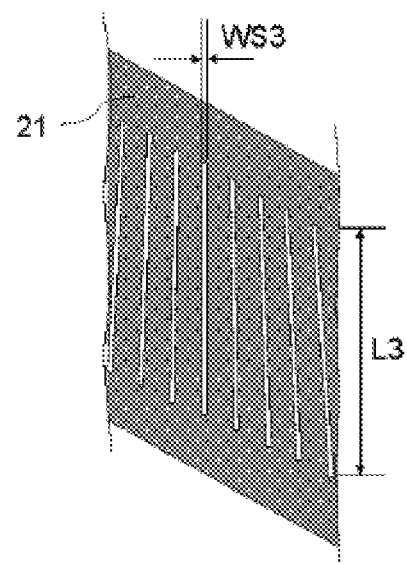

FIGS. 4A and 4B are schematic perspective views illustrating an example of the structure of the collimator 1. FIG. 4A is a schematic perspective view illustrating an example of the structure of an assembled collimator 1. FIG. 4B is a schematic exploded view of the collimator 1 of FIG. 4A. As shown in FIG. 4A, the collimator 1 includes a plurality of plate parts 11 and 21 forming a lattice structure. In FIGS. 5A and 5B, in order to simplify explanation, only relevant portions of the plate parts 11, 21 are shown in the figure. FIGS. 5A and 5B are schematic diagrams illustrating an example of the plate-shaped parts that form the collimator; FIG. 5A is a diagram illustrating the plate-shaped part 11, and FIG. 5B is a diagram illustrating the plate-shaped part 21.

As shown in FIGS. 4A and 4B and FIGS. 5A and 5B, the collimator 1 has a plurality of plate-shaped parts 11 (corresponding to an example of the first plate-shaped parts), and a plurality of plate-shaped parts 21 (corresponding to an example of the second plate-shaped parts) arranged in a direction crossing the first plate-shaped parts 11. Each of the first plate-shaped parts 11 and the second plate-shaped parts 21 include a spacing between each other as well as a spacing between adjacent plate-shaped parts 11, 21. The spacing between plate-shaped parts 11, 21 define the divisions 1a (shown in FIG. 2) of the collimator 1.

Referring to FIGS. 4A and 4B, each first plate-shaped part 11 includes a first slotted plate part 11a having a plurality of slits S1 having one side of each of the slits S1 open (corresponding to an example of the first slits) formed thereon with a spacing therebetween, a second slotted plate part 11b arranged on the side opposite the slits S1 of the first slotted plate part 11a and having a plurality of slits S2 having one side of each of the slits S1 open (corresponding to an example of the second slits) formed thereon with a spacing therebetween, and an adjustment plate part 11c arranged between the first slotted plate part 11a and the second slotted plate part 11b. The adjustment plate part 11c may comprise a spacer plate configured to maintain spacing between the first slotted plate part 11a and the second slotted plate part 11b.

For the first plate-shaped part 11, supposing that the width of the first plate-shaped part 11 is W1, the width W2 of the second plate-shaped part 21 may be the same.

The number of the plural slits S1 and slits S2 formed on the first and second slotted plate parts 11a, 11b may correspond to the number of the plate-shaped parts 21 to be received therein.

Referring to FIGS. 4B and 5A, the widths WS1, WS2 of the plural slits S1, S2 of the first and second slotted plate parts 11a and 11b are slightly larger than the thickness of the plate-shaped part 21. The lengths L1, L2 of the plural slits S1, S2 may be about half of the widths W1a, W1b of the first and second slotted plate parts 11a and 11b. In this embodiment, the lengths L1, L2 of the plural slits S1, S2 are about half the widths W1a, W1b of the first and second slotted plate parts 11a and 11b. However, the length to width relationship is not limited to this as the lengths L1, L2 of the plural slits S1, S2 may also be longer with consideration to maintenance of the mechanical strength of the first and second slotted plate parts 11a and 11b. Also, the lengths L1, L2 of the plural slits S1, S2 may be formed shorter considering mechanical strength is not compromised.

Here, the plural slits S1, S2 of the first and second slotted plate parts 11a and 11b are formed obliquely at an angle corresponding to a common point outside of the collimator 1, which may be the position of the focal point of the X-ray source (i.e., X-ray bulb 101). Consequently, as the plural slits S1, S2 have the plate-shaped parts 21 fit in them, the plate-shaped parts 21 can be automatically and/or mechanically inclined at an angle corresponding to the position of the focal point of the X-ray source upon assembly thereof.

Figure 6A:
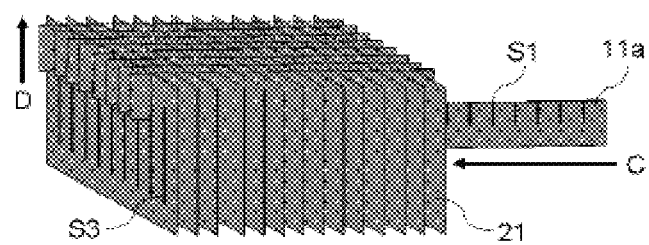
FIGS. 6A to 6C are schematic perspective views illustrating an example of a manufacturing method of the collimator of FIGS. 4A and 4B.
Figure 6B:
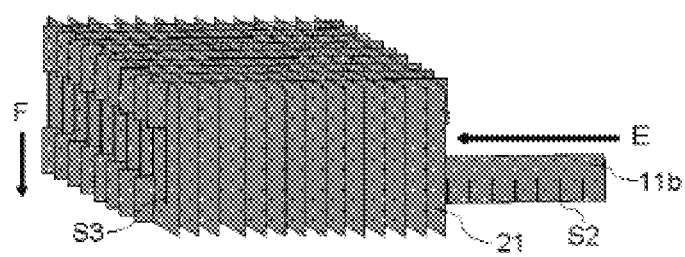
Figure 6C:
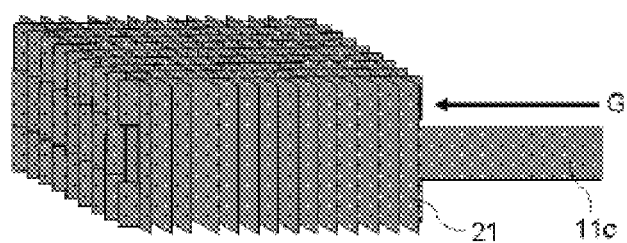

Referring to FIGS. 4b and 6C, the adjustment plate part 11c is arranged between the first and second slotted plate parts 11a and 11b, and facilitates fitting and holding the first slotted plate part 11a as well as the second slotted plate part 11b with the plate-shaped part 21. Consequently, the width W1c of the adjustment plate part 11c is selected to be appropriate to come in contact with the edges of the first and second slotted plate parts 11a and 11b. As shown in FIG. 6C, the gap formed when the first and second slotted plate parts 11a, 11b are fit in slits to a plurality of slits S3 of the plate-shaped part 21 is almost equal to the width W1c of the adjustment plate part 11c. In this embodiment, only one adjustment plate part 11c is arranged between the first and second slotted plate parts 11a and 11b. However, multiple adjustment plate parts may be used between the first and second slotted plate parts 11a and 11b.

Referring to FIGS. 4B and 5B, on the second plate-shaped part 21, the plural slits S3 (corresponding to an example of the third slits) and are formed with a spacing between them. The plural slits S3 are internal to the second plate-shaped part 21 (i.e., closed). The plural slits S3 are formed with a certain spacing from the peripheral edge e of the second plate-shaped part 21. Also, the number of the plural slits S3 may be equal to the number of the first plate-shaped parts 11 to be received therein. The plural slits S3 are also formed with a certain spacing therebetween that corresponds to the divisions 1a of the collimator 1.

For each second plate-shaped part 21, the width WS3 of each of the plural slits S3 is slightly larger than the thickness of the plate-shaped part 11. The length L3 of each of the plural slits S3 may be a length obtained by subtracting the lengths L1, L2 of the plural slits S1, S2 of the first slotted plate part 11a and the second slotted plate part 11b from the width W1 of the plate-shaped part 11.

Also, the plural slits S3 are formed in the second plate-shaped part 21 to be inclined at an angle corresponding to a common point, such as the same common point corresponding to the angle of the plural slits S1, S2 of the first and second slotted plate parts 11a and 11b. The common point may be the position of the focal point of the X-ray source. Consequently, as the first plate-shaped parts 11 are fit in the plural slits S3 of the second plate-shaped part 21, the first plate-shaped part 11 becomes automatically and/or mechanically inclined at an angle corresponding to the position of the focal point of the X-ray source.

In this case, at the position where the first plate-shaped part 11 and the second plate-shaped part 21 intersect, the plural slits S1, S2 and the plural slits S3 are adjacent to each other while edges of the second plate-shaped part 21 and the first plate-shaped part 11 are loosely fit together during this assembly stage. That is, the second plate-shaped part 21 is positioned with the slits S1 of the first slotted plate part 11a on the side of one peripheral edge e of the second plate-shaped part 21 without the slits S3, and the second plate-shaped part 21 is positioned with the slits S2 of the second slotted plate part 11b on the side of the opposite peripheral edge e without the slits S3. In this way, the first plate-shaped parts 11 and the second plate-shaped parts 21 are arranged crossing each other in a grid-like pattern forming a substantially perpendicular junction therebetween, which forms the divisions 1a (shown in FIG. 2) with the adjacent edges of the second plate-shaped part 21 and the first plate-shaped part 11. The assembly of the structure in this manner enables adjustment of each of the first plate-shaped part 11 within each of the slots S3 during further assembly procedures.

In this way, as the plural slits S3 of the second plate-shaped parts 21 are formed with a certain spacing from the peripheral edge e of the plate-shaped part 21, when they are fit with the first plate-shaped parts 11, it is possible to easily position the plate-shaped parts 11 within the respective slits S3. Consequently, it is possible to suppress deformation of the plate-shaped part 11 to ensure stable fitting, so that assembly of the structure can be structurally stable as well as assembled with a high precision.

In this embodiment, the first plate-shaped parts 11 and the second plate-shaped parts 21 are anchored with each other as they are arranged. However, it is not limited to this scheme. Here, by setting the first plate-shaped parts 11 and the second plate-shaped parts 21 so that they are fixed with each other, the influence of oscillation, vibration, or other movement, etc., can be minimized.

In the following, the manufacturing method of the collimator according to this embodiment will be explained with reference to an example. First of all, the first plate-shaped parts 11 and second plate-shaped parts 21 are formed. That is, the first and second slotted plate parts 11a, 11b having plural slits S1, S2 inclined at an angle corresponding to the position of the focal point of the X-ray source and adjustment plate part 11c are formed. Also, plate-shaped parts 21 having plural slits S3 inclined at an angle corresponding to the position of the focal point of the X-ray source are formed. Thus, the plurality of first plate-shaped parts 11 as well as the plurality of second plate-shaped parts 21 form divisions 1a that are directed to a common point outside of the collimator 1.

Blanks of the first and second slotted plate parts 11a, 11b of the first plate-shaped parts 11 and the second plate-shaped parts 21 are cut out from a plate-shaped material with excellent X-ray shielding characteristics.

Plural slits S1, S2 having the proper shapes and dimensions are formed on the blanks of the first plate-shaped parts 11, and slits S3 with the proper shape and dimensions are formed on the blanks of the second plate-shaped parts 21.

The collimator 1 has a lattice structure composed of plate-shaped parts 11, 21. Here, when the collimator 1 is set at the proper position in the X-ray CT device, the divisions of the lattice structure should be arranged so that they face the focal point of the X-ray bulb 101 (i.e., X-ray source). Consequently, the slits S1, S2 of the first plate-shaped parts 11 and the slits S3 of the second plate-shaped parts 21 should be formed in the proper shapes and dimensions to form the collimator 1 with an arc shape.

In this case, examples of the materials with X-ray shielding characteristics include W (tungsten), Mo (molybdenum), Ta (tantalum), Pb (lead), and alloys containing at least one of the heavy metals. However, it is not limited to these types of materials. Appropriate types of materials with excellent X-ray shielding characteristics may be selected.

Formation of the slits S1, S2, S3 maybe carried out using the etching method. However, it is not limited to this scheme.

The first plate-shaped parts 11 and second plate-shaped parts 21 are assembled crossing each other. First of all, as shown in FIG. 6A, the first slotted plate parts 11a of the first plate-shaped parts 11 are inserted in the C-direction into the plural slits S3 of the second plate-shaped parts 21. In this case, the plural slits S1 of the first slotted plate parts 11a are oriented towards the side of one peripheral edge e of the plate-shaped part 21 where the slits S3 are not arranged. The plural slits S1 and slits S3 are then aligned, and the first slotted plate parts 11a are moved in the D-direction, so that the first slotted plate parts 11a and the plate-shaped part 21 are fit with each other.

As shown in FIG. 6B, the second slotted plate parts 11b of the first plate-shaped parts 11 are inserted in the E-direction into the plural slits S3 of the plate-shaped parts 21. In this case, the plural slits S2 of the second slotted plate parts 11b are oriented towards the side of the plate-shaped part 21 on the other peripheral edge e where the slits S3 are not arranged. Then, the plural slits S2 and S3 are aligned and the second slotted plate parts 11b are moved in the F-direction, respectively, and the second slotted plate parts 11b and the plate-shaped parts 21 are then fit with each other.

Finally, as shown in FIG. 6C, the adjustment plate parts 11c of the first plate-shaped parts 11 are inserted in the G-direction into the plural slits S3 of the second plate-shaped parts 21, so that they are arranged between the first and second slotted plate parts 11a, 11b.

In this way, when the plural slits S1, S2 inclined at an angle of the first plate-shaped parts 11 are fit with the plural slits S3 inclined at an angle of the second plate-shaped parts 21, it is possible to perform fitting while also aligning. Consequently, it is possible to suppress deformation of the first plate-shaped parts 11, and to perform fitting with a high stability. As a result, it is possible to assemble at a high precision.

According to the collimator, manufacturing method of the collimator, and X-ray CT device presented as an example, it is possible to suppress deformation of the first plate-shaped parts 11 and to make a stable fitting, so that it is possible to carry out assembly with a high precision. As a result, it is possible to suppress X-rays from passing through the gaps of the plural slits S1, S2, S3. Consequently, the desired X-rays can be incident on the scintillators 4 arranged in the various divisions 1a, so it is possible to carry out measurement at an even higher precision.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A collimator, comprising:
a plurality of first plate-shaped parts; and
a plurality of second plate-shaped parts interlocking with the plurality of first plate-shaped parts, each of the plurality of first plate-shaped parts and the plurality of second plate-shaped parts arranged with a spacing therebetween and forming a grid-like pattern, wherein:
each of the plurality of first plate-shaped parts comprises a first slotted plate part having a plurality of first slits formed thereon that is fixed to each of the plurality of second plate-shaped parts;
a second slotted plate part having a plurality of second slits formed thereon is coupled to a side of the second plate-shaped parts opposite to the first slotted plate part, and;
an adjustment plate part is disposed between the first slotted plate part and the second slotted plate part; wherein
each of the plurality of second plate-shaped parts includes a plurality of closed slits formed therein for receiving each of the first slotted plate part and the second slotted plate part.

2. The collimator of claim 1, wherein a length of each of the plurality of closed slits is obtained by subtracting a length of one of the plurality of first slits of the first slotted plate part from a width of the first slotted plate part to find a first difference, subtracting a length of one of the plurality of second slits of the second slotted plate part from a width of the second slotted plate part to find a second difference, and adding the first and second differences to a width of the adjustment plate.

3. The collimator of claim 1, wherein a length of the plurality of first slits is one half of a width of the first slotted plate part.

4. The collimator of claim 3, wherein a length of the plurality of second slits is one half of a width of the second slotted plate part.

5. The collimator of claim 1, wherein the plurality of first slits and the plurality of second slits are angled to position each of the plurality of first plate-shaped parts and the plurality of second plate-shaped parts toward a common point outside of the collimator.

6. The collimator of claim 1, wherein the adjustment plate part contacts edges of both of the first slotted plate part and the second slotted plate part.

7. An X-ray CT device, comprising:
a lattice structure comprising a material that substantially prevents transmission of X-rays, the lattice structure comprising a plurality of first plate-shaped parts disposed orthogonally to a plurality of second plate-shaped parts, each of the plurality of first plate-shaped parts interlocking with each of the plurality of second plate-shaped parts and defining a grid-like pattern of rectangular openings that are oriented toward a common point outside of the lattice structure, wherein:
each of the plurality of first plate-shaped parts comprises a first slotted plate part having a plurality of first slits formed thereon that is fixed to each of the plurality of second plate-shaped parts;
a second slotted plate part having a plurality of second slits formed thereon is coupled to a side of the second plate-shaped parts opposite to the first slotted plate part, and;
an adjustment plate part is disposed between the first slotted plate part and the second slotted plate part; wherein
each of the plurality of second plate-shaped parts includes a plurality of closed slits formed therein for receiving each of the first slotted plate part, the second slotted plate part, and the adjustment plate part therein.

8. The X-ray CT device of claim 7, wherein a length of each of the plurality of closed slits is obtained by subtracting a length of one of the plurality of first slits of the first slotted plate part from a width of the first slotted plate part to find a first difference, subtracting a length of one of the plurality of second slits of the second slotted plate part from a width of the second slotted plate part to find a second difference, and adding the first and second differences to a width of the adjustment plate.

9. A method for manufacturing a collimator, the method comprising:
forming a plurality of first plate-shaped parts, each of the plurality of first plate-shaped parts comprising a first slotted plate part having a plurality of first slits formed thereon and a second slotted plate part having a plurality of second slits formed thereon;
forming a plurality of second plate-shaped parts having a plurality of closed slits formed thereon;
inserting each of the first slotted plate part and the second slotted plate part into each of the plurality of closed slits of the second plate-shaped parts; and
inserting an adjustment plate into each of the plurality of closed slits of the second plate-shaped parts in a position between each of the first slotted plate part and the second slotted plate part to form a lattice structure.

10. The method of claim 9, wherein the lattice structure comprises a grid-like pattern of rectangular openings formed between adjacent first plate-shaped parts and second plate-shaped parts.

11. The method of claim 10, wherein each of the rectangular openings are oriented toward a common point outside of the lattice structure.

12. The method of claim 9, wherein a length of each of the plurality of closed slits is obtained by subtracting a length of one of the plurality of first slits of the first slotted plate part from a width of the first slotted plate part to find a first difference, subtracting a length of one of the plurality of second slits of the second slotted plate part from a width of the second slotted plate part to find a second difference, and adding the first and second differences to a width of the adjustment plate.

* * * * *